United States Patent [19]

Golias et al.

[11] Patent Number: 5,400,923
[45] Date of Patent: * Mar. 28, 1995

[54] APPARATUS FOR DISCHARGING CONTENTS OF A SEALED CONTAINER

[75] Inventors: Tipton L. Golias; Robert J. Sarrine; Joseph H. Golias; Ronald A. Mayes, all of Beaumont, Tex.

[73] Assignee: Helena Laboratories Corporation, Beaumont, Tex.

[*] Notice: The portion of the term of this patent subsequent to May 19, 2009 has been disclaimed.

[21] Appl. No.: 504,597

[22] Filed: Apr. 4, 1990

Related U.S. Application Data

[63] Continuation-in-part of Ser. No. 208,447, Jun. 20, 1988, abandoned, and a continuation-in-part of Ser. No. 382,760, Jul. 21, 1989, Pat. No. 5,114,033.

[51] Int. Cl.⁶ ........................ B67D 5/00; A61M 5/178
[52] U.S. Cl. ........................ 222/82; 222/85; 222/89; 222/479; 222/211; 222/400.8; 222/633; 604/201; 604/217
[58] Field of Search .................. 222/80-86, 222/209, 211, 401, 410.8, 400.7, 464, 478, 481.5, 633, 188, 396, 397; 215/307, 309-311; 141/50, 55, 57, 58

[56] References Cited

U.S. PATENT DOCUMENTS

| | | | |
|---|---|---|---|
| 380,041 | 3/1888 | Kneuper | 222/209 |
| 706,806 | 8/1902 | DeForest | 222/209 |
| 849,772 | 4/1907 | Cordeaux | 222/400.8 |
| 858,863 | 7/1907 | Farrand | 222/400.8 |
| 935,094 | 9/1909 | DeVilbiss | 215/309 |
| 947,468 | 1/1910 | Fish | 222/400.8 |
| 1,577,539 | 3/1926 | Polk | 215/309 |
| 1,669,776 | 5/1928 | Osburn . | |
| 2,098,160 | 11/1937 | Peuitt | 222/209 |
| 2,431,596 | 11/1947 | Wickstrum | 222/209 |
| 2,612,998 | 10/1952 | Smith | 222/464 |
| 2,740,555 | 3/1956 | Howden | 222/89 |
| 2,965,255 | 12/1960 | Gerarde . | |
| 3,160,330 | 12/1964 | Pollitt | 222/209 |
| 3,160,330 | 12/1964 | Pollitt | 222/209 |
| 3,208,639 | 9/1965 | Marwell et al. | 222/82 |
| 3,230,954 | 1/1966 | Burgess et al. | 215/247 |
| 3,312,376 | 4/1967 | Rooney | 222/479 X |
| 3,596,673 | 8/1971 | Laucournet . | |
| 3,707,239 | 12/1972 | Harris, Sr. et al. | 215/247 |
| 3,823,718 | 7/1974 | Tromovitch | 222/397 X |
| 3,837,376 | 9/1974 | Brown et al. | 422/100 |
| 3,872,730 | 3/1975 | Ringnose et al. | 73/421 |
| 3,972,812 | 8/1976 | Gresl, Jr. | 210/782 |
| 3,985,032 | 10/1976 | Avakian . | |
| 3,994,423 | 11/1976 | Burg | 222/420 |
| 4,043,341 | 8/1977 | Tromovitch | 222/470 X |
| 4,186,882 | 2/1980 | Szczepanski | 222/479 X |
| 4,203,840 | 5/1980 | Stoeppler et al. | 422/101 |
| 4,228,831 | 10/1980 | Kerns . | |
| 4,262,671 | 4/1981 | Kersten . | |
| 4,296,786 | 10/1981 | Brignola | 222/83.5 X |
| 4,461,406 | 7/1984 | Vannucci | 222/211 |
| 4,530,466 | 7/1985 | Rounkles et al. | 222/211 X |
| 4,784,299 | 11/1988 | Stenger | 222/397 |
| 4,808,381 | 2/1989 | McGregor et al. | 222/83.5 X |
| 5,033,653 | 7/1991 | Kaufman | 222/185 |

FOREIGN PATENT DOCUMENTS

| | | | |
|---|---|---|---|
| 348116 | 12/1989 | European Pat. Off. . | |
| 108754 | 6/1985 | Japan | 73/863.01 |
| 278713 | 10/1951 | Switzerland . | |
| 506779 | 2/1938 | United Kingdom . | |

Primary Examiner—Andres Kashnikow
Assistant Examiner—Kenneth DeRosa
Attorney, Agent, or Firm—Spencer, Frank & Schneider

[57] ABSTRACT

A pump for discharging the contents of a sealed container, such as a test tube, is connected to a body member which includes an inlet path and a discharge path with a delivery tube in the discharge path. A predetermined clearance is provided between the exterior of the delivery tube and the interior of the discharge path, the clearance providing venting, or blow-by, such that temperature changes do not cause accidental discharge of the contents of the container, while still maintaining sufficient resistance to venting for permitting pressurizing the interior of the test tube with the pump for accurately controlling the discharge of the test tube contents. A second or supplemental vent is provided in the pump.

20 Claims, 1 Drawing Sheet

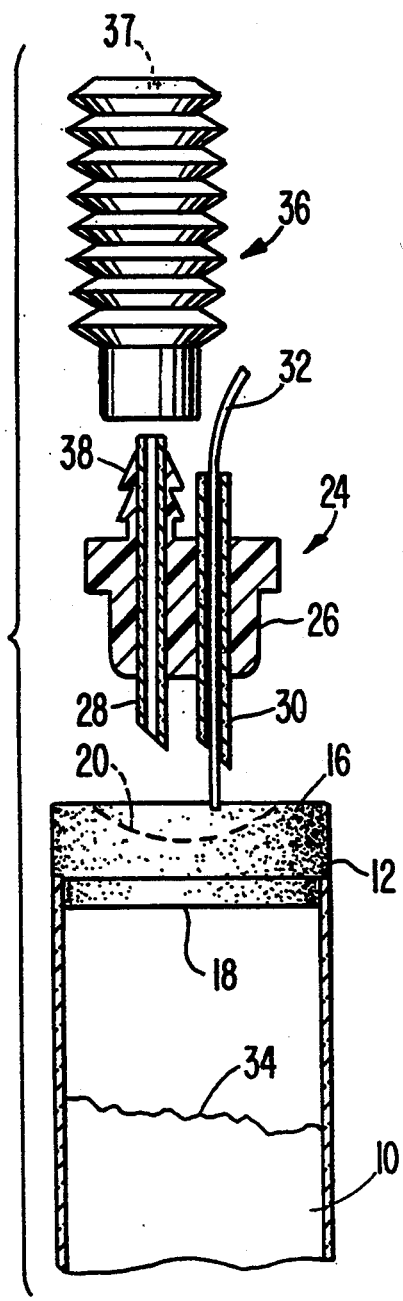
FIG. 1.
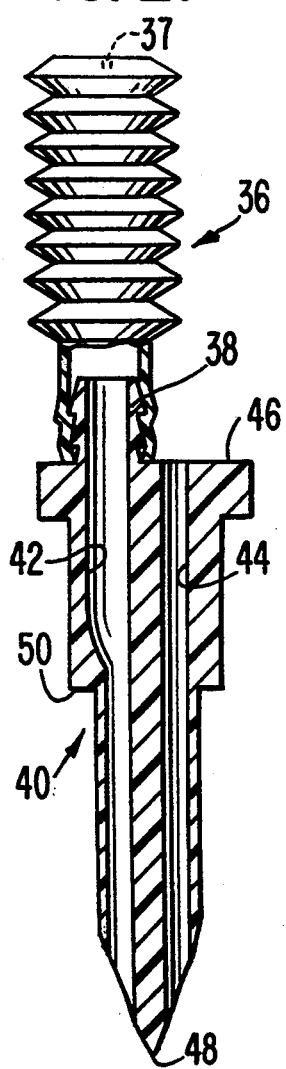
FIG. 2.
FIG. 3.
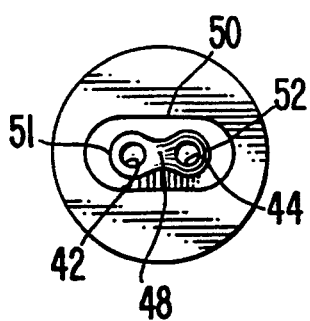
FIG. 4.
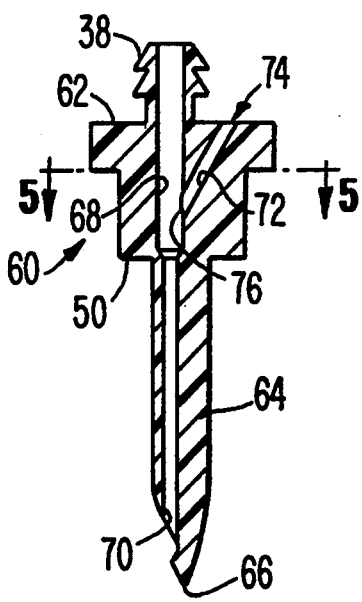
FIG. 5.
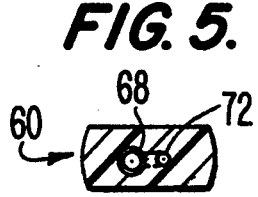
FIG. 6.
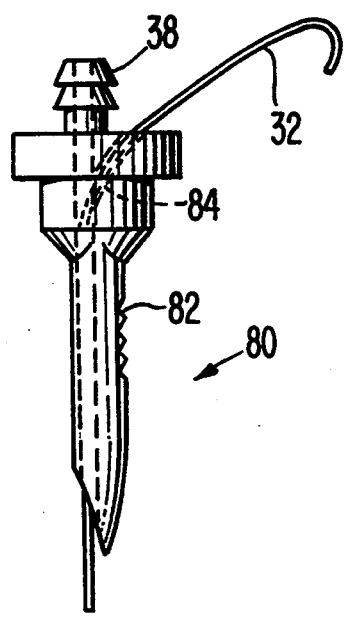

APPARATUS FOR DISCHARGING CONTENTS OF A SEALED CONTAINER

This application is a continuation-in-part of application Ser. No. 07/208,447, filed Jun. 20th, 1988, now abandoned, and a continuation-in-part of application Ser. No. 07/382,790, filed Jul. 21st, 1989, now U.S. Pat. No. 5,114,003.

CROSS REFERENCE TO RELATED APPLICATIONS

Some of the subject matter disclosed in the present application is common to the earlier co-pending application of Tipton Golias, application Ser. No. 07/208,447, filed Jun. 20th, 1988 and assigned to the Assignee of the present invention, and to the earlier application of Tipton Golias, et al, application Ser. No. 07/382,760, filed Jul. 21st, 1989, and assigned to the Assignee of the present invention, both of which are incorporated herein by reference.

BACKGROUND OF THE INVENTION

The present invention relates generally to an apparatus for discharging the contents of a sealed container and has particular utility in discharging the contents of a test tube, serum collection tube or the like.

Test tubes are frequently used as collection containers for blood specimens and the like. Typically, an anticoagulant is placed in the test tube, then a blood specimen is withdrawn from a patient and placed into the test tube, and then the test tube sealed with a resilient closure or stopper which is typically formed of rubber. The test tube and its contents are thereafter subjected to temperature variations as well as centrifuging operations. Prior to the invention described in the earlier of the aforementioned co-pending applications, after centrifuging, it was typical to remove the stopper from the test tube such that some of the contents could be transferred to a specimen plate or the like for analysis.

There were, of course, numerous problems associated with the removal of the stopper from the test tube such as the potential for contamination of the blood and exposure of the laboratory technician to any diseases carried by the blood. Of course, there is substantial present concern by the laboratory technician because of potential exposure to the HIV virus, hepatitis or other diseases which may be carried by the blood. The earlier of the prior applications describes a first solution to the aforementioned problem by the provision of a method and apparatus for discharging the contents of a sealed container which includes, in general terms, a holder containing two cannulas, or needles, which are utilized to puncture the rubber stopper or closure of the test tube. One of the cannulas is connected to a compressible bulb or pump, and a delivery tube is inserted through the second cannula into the interior of the test tube. Then, upon compressing the bulb, air is introduced into the test tube and the contents of the test tube are pressurized and thus, partially discharged through the delivery tube onto a specimen plate.

The second of the two copending prior applications discloses several improvements in the various components which produce numerous advantages.

Prior to the invention, however, several concerns became apparent. One concern was the degree of force required on the pump or bulb mechanism in order to cause one or more droplets to be discharged. Thus, the laboratory technician desired the ability to actuate the pump only once and, in response, a single droplet would be discharged. But it was also required that air be able to enter the interior of the sealed test tube after the droplet was discharged for two reasons, namely, first, to avoid creating a reduction in pressure or partial vacuum within the test tube and second, to fill the compressible bulb so that a second droplet could be discharged.

Yet a second problem arose because collection tubes of the type heretofore described frequently undergo temperature changes or variations in excess of 30 degrees Celsius. For example, a sealed collection tube containing blood is frequently refrigerated, tending to cause a pressure decrease within the collection tube. In a laboratory, after removal from a refrigerator, the temperature of the contents of the collection tube may increase to room temperature or, if positioned in direct sunlight, to an even greater temperature, thus tending to cause a pressure increase and even an accidental discharge of the test tube contents.

SUMMARY OF THE INVENTION

The present invention provides an improvement in an apparatus for transferring fluid from a test tube or the like, where the test tube includes a resilient, self-sealing reusable puncturable closure. Means are provided for puncturing the test tube closure for establishing a fluid inlet path and a fluid discharge path. A delivery tube extends through the discharge path. A compressible bulb or bellows is provided on the inlet path and when the bellows is actuated, the interior of the test tube is pressurized thus causing fluid from the test tube to be discharged through the fluid discharge path.

We have discovered that it is necessary to provide some clearance, or venting, between the interior and exterior of the sealed test tube. Preferably the venting is between the outside diameter of the delivery tube and the interior of the cannula, or conduit, through which the delivery tube is positioned. Then, of course, as the test tube undergoes temperature changes, air can be drawn into or expelled out of the interior of the test tube. However, the clearance cannot be large, otherwise in response to compressing the bulb or pump, too much air would pass through this clearance, thus reducing the pumping efficiency. In fact, if the clearance was excessive, then no fluid would be discharged. This phenomenon is referred to as "blow-by". If the clearance is larger than necessary, then repeated pumping and/or excessive force is required on the pump in order to discharge fluid from the test tube through the delivery tube to a specimen plate. Hence, it is necessary to minimize the clearance, thus yielding a discharge or delivery system which is extremely responsive to the pressure on the pump mechanism. Thus the present invention provides a clearance between the exterior of the delivery tube and the interior of the discharge path for venting the interior of the test tube in response to temperature variations. Because blood or serum may tend to obstruct part of the clearance, a supplemental vent is provided in the bellows.

Yet another consideration which has developed subsequent to the invention described in the earlier prior application is a desire to facilitate insertion of the apparatus into the rubber closure or stopper of the test tube. We have discovered that while the prior approach is functional, a new and improved approach provides additional benefits as will be described.

The present invention provides an improved apparatus for discharging the contents of a sealed test tube which permits better control of the rate and amount of discharge, accommodates changes in temperature of the test tube and its contents and also provides for easier insertion of the apparatus through the resilient rubber closure, or stopper, of the test tube.

BRIEF DESCRIPTION OF THE DRAWINGS

The various features, objects and benefits of the present invention, together with additional benefits which will be attained by its use, will become more apparent upon reading the following detailed description of the invention taken in connection with the drawings.

In the drawings, wherein like reference numerals identify corresponding components:

FIG. 1 is an exploded illustration, partly in section, of a portion of a test tube, a test tube stopper and the apparatus of the present invention;

FIG. 2 is an illustration, partly in section, of a second form of the apparatus of the present invention;

FIG. 3 is a bottom view of the apparatus of FIG. 2;

FIG. 4 is a partial, sectional illustration of a preferred embodiment of the present invention;

FIG. 5 is a sectional view as seen in the direction of arrows 5—5 of FIG. 4; and FIG. 6 is a partial elevation view of an alternate embodiment of the present invention.

DETAILED DESCRIPTION OF THE INVENTION

With reference to the drawings, and more particularly FIG. 1, a container 10 is partially illustrated and should be understood to refer to a conventional test tube, serum collection tube or the like. Thus, the container 10, which will be referred to as a test tube, is formed as an elongated member with a hollow interior having a thin wall, an open first end 12 and typically a closed, rounded second end, or bottom (not shown). A test tube of this nature is typically circular in cross section although other cross sectional configurations may be utilized.

The test tube 10 has its end 12 closed by a resilient, self-sealing, reusable closure, or stopper, 14 which would also be of circular cross section (in plan view), having an enlarged head 16 and a stem 18 such that the stopper is of generally "T" shape when viewed in a cross section through a vertical plane. The stopper is configured to frictionally, resiliently sealingly engage the interior of the wall of the test tube 10 at the end 12, as well as engage the test tube rim, as is conventional. Also, as is conventional, the top central portion of the stopper head may include a slight concavity, or recess, 20.

Means are provided for discharging the contents of the sealed test tube 10 without removing the stopper 14, and means are provided for establishing a fluid inlet path and a fluid discharge path. The two fluid paths are established by puncturing the stopper 14. Then by connecting a pump to one end of the input path and actuating the pump, the interior of the test tube may be slightly pressurized to cause fluid to flow through the discharge path. In the embodiment of FIG. 1, means 24 is provided for establishing a fluid inlet path and a fluid discharge path. The fluid flow path establishing means 24 includes a body member 26 having two bores therethrough. Each bore is fitted with a hollow needle, or cannula, 28, 30, respectively, and each cannula has a tapered, or sharpened, end positioned to puncture, or pierce, the head 16 of the stopper 14 as the body 26 is moved toward the stopper 14.

A delivery tube, or the like, 32 is inserted through the needle 30, and the delivery tube is slidable within the needle 30 such that after needles 28 and 30 penetrate through, or pierce, the stopper,, a delivery tube 32 may be inserted into the needle 30 and moved into the fluid 34.

A pump means 36 is connected to the needle 28 such that upon actuating the pump means, air is introduced through the interior of the needle 28 to slightly pressurize the interior of the test tube, thus forcing a droplet of fluid 34 to be forced through the delivery tube 32 to thus be discharged onto a specimen plate or the like. The tube 32 may be extended into the fluid 34 to a desired depth to access different levels of fluid within the tube. The pump means 36 which is provided at one end of the needle 28, may be a bellows, as illustrated, or other form of resiliently compressible bulbous member.

At one end of the body member 26, preferably the end opposite the sharpened points of the needles, a plurality of barbs 38, of generally circular cross section, are provided for securing the pump means, or bellows, 36 to the body.

According to the principles of the present invention, we have discovered that a certain clearance is necessary between the outside or exterior diameter of the delivery tube 32 and the interior of the needle 30 for the purpose of venting the interior of the test tube. In the embodiment of FIG. 1, the needles are hollow and of circular cross section and the delivery tube is hollow and of circular cross section. According to the principles of the present invention, if the interior diameter of the discharge path, or needle 30, is 0.045 inches, then the optimum, outside diameter of the delivery tube 32 should be 0.044 inches. Thus, the clearance would be 0.001 inches, in diameter. The $$\pi \frac{(D_2 - D_1)^2}{4}$$

where $D_2 = 0.045$ inches and $D_1 = 0.044$ inches. cross sectional clearance area may be calculated as While this appears to be an optimal clearance, satisfactory results have been obtained with a slightly larger clearance, as well as with a slightly smaller clearance. However, as the clearance increases, there is a loss of the ability to pressurize the interior of the test tube. Stated alternatively, there is excessive leakage of air in response to actuation of the pump means, and, as a consequence, additional pressure is required to discharge fluid. This additional pressure may be supplied by either applying greater force to the pump means or by repeatedly activating the pump means, but in either event, there is a reduction in the ability to control the fluid discharge. Also, as the clearance decreases, there is insufficient venting as the test tube with fluid therein is subjected to temperature differentials. Thus, it is important to balance these considerations to provide venting while maintaining the ability to pressurize the test tube.

We have further discovered that depending upon the nature of the fluid within the test tube, some fluid may tend to obstruct the clearance or vent between the exterior of the delivery tube and the interior of the fluid discharge path. We have discovered that an additional, supplemental venting means is often necessary. In a preferred embodiment, a small aperture 37 in the top of the bellows or compressible pump functions as a vent to enable additional air to enter into, or escape from, the interior of the test tube. When it is desired to discharge fluid, the aperture may be conveniently covered or closed, such as with the hand of the laboratory technician using the apparatus. Thus the aperture when closed does not adversely affect the ability of the apparatus to pressurize the interior of the test tube for discharging the fluid contents. The aperture may be considered as part of a venting means.

Referring next to FIGS. 2 and 3, an alternate form of the present invention will now be described. The means 24 for establishing the first and second fluid flow paths, or the inlet and discharge paths, within the stopper 14 of the test tube is illustrated as including an elongated body member 40 being of circular configuration at one end to which the pump means, or bellows, 36 is attached. The body member has two circular bores 42, 44, respectively, therethrough corresponding to the bores of the needles 28 and 30 in the embodiment of FIG. 1. Hence, the two bores 42, 44 extend through the length of the body 40, and are generally parallel to each other and parallel to the elongated axis of the body. The exterior diameter and configuration of the body changes from a first end 46 where the bellows is attached toward the second end or tip 48. Specifically, the cross section is circular but approximately at the mid point 50 along the length of the body, the cross sectional configuration becomes generally flat and blade-like, with curved sides 51, 52. Thus, the body member 40 of FIGS. 2 and 3 may be considered as a self-contained spike for piercing the rubber stopper of the test tube. By locating the pointed tip 48 generally centered between the lateral extremities of the body (e.g., as seen from the bottom), the body member 40 will self-center as it is inserted through the rubber stopper 14.

The bellows, or pump, is attached to one end of one bore 42, which functions as the input bore, and a delivery tube 32 is inserted through the discharge bore 44. Hence, the diameter of the discharge bore 44 should be slightly greater than the outside diameter of a delivery tube 32, to thus provide the desired venting clearance.

The embodiment of FIG. 1 has heretofore been commercialized by the assignee of the present invention. Referring next to FIGS. 4 and 5, a preferred embodiment of the present invention, which will subsequently be commercialized, is illustrated, including means 60 for puncturing the stopper and for establishing the fluid inlet path and the fluid discharge path. The means 60 for establishing the fluid flow paths is an elongated spike having a head 62 of circular cross section, and the cross section thereafter gradually tapering to a thin, flat blade-like portion 64 culminating in a puncturing tip 66 at the end opposite the head 62. Barbs 38 are provided to facilitate securing a pump means to the body 60. A bore 68 of circular cross section is provided through the spike with one end of the bore 68 extending interiorly of the barbs 38. The pump means or bellows is secured to the inlet path and is secured to the barbs 38. The opposite end 70 of the bore is positioned adjacent the pointed tip 66. The tip is centered, laterally to provide for selfcentering of the spike as it is inserted into the stopper. A second, straight bore 72 is provided in the body at an angle relative to the longitudinal axis of the bore 68, the bore 72 having one end 74 opening into the head 62 of the spike, and the opposite end 76 intersecting the bore 68. In the embodiment of FIGS. 4 and 5, the delivery tube 32 is inserted through the bore 72, and thereafter, where the bore 72 intersects the bore 68 as at 76, the delivery tube 32 extends through the bore 68 beyond the bore end 70 and beyond the tip 66 into the fluid within the test tube. Thus, the bore 68 must be sufficiently large, in diameter, to accommodate the diameter of the delivery tube 32 and to allow air to be introduced into the interior of the test tube 10 in response to pressure on the bellows, or pump means, 36. In addition, there must be a venting means or clearance between the outside diameter of the delivery tube 32 and the inside diameter of the discharge path along the entire length of the bore 72, and along bore 68 from its intersection 76 to the bore end 70. The embodiment of FIG. 4, when compared to the embodiment of FIG. 2, provides a second bore 72 in FIG. 4 which is relatively short in length, thus permitting a smaller thickness blade portion 64 as well as being easier to manufacture. In the embodiment of FIG. 4, a portion of the inlet and outlet paths may be considered coextensive and, with the delivery tube properly inserted, a portion of the inlet and outlet paths are concentric. It is contemplated that the venting means for the embodiment of FIG. 4 will include the aperture in the bellows.

The generally squared-off mid-point 50 of the body member 40 of FIG. 2 and the corresponding portion of the member 60 of FIG. 4 provide an additional benefit. During manufacture of the apparatus of the present invention, the spikes 48, 66 or pointed, sharpened cannulas 28, 30 may be inserted into a material such as Styrofoam, which is a Dow Chemical Company trademark for an expanded rigid polystyrene, for protection. The squared-off mid-points limit the depth of the insertion into the Styrofoam. When a plurality of body members are aligned in a row within a Styrofoam block, the feature of inserting all the body members to the same depth enables the entire row of body members to be loaded into an insertion machine for automatically inserting the puncturing mechanisms into test tubes. Hence, the squared-off mid-points function as a locator for subsequent insertion of the puncturing mechanism.

Referring now to FIG. 6, yet another embodiment of the present invention is illustrated wherein means 80 for establishing the fluid paths is provided generally similar to the fluid flow path establishing means of the embodiment of FIGS. 4 and 5. One difference, however, is that on the exterior of the blade-like portion 64, there are a plurality of serrations, teeth or barbs 82. Hence, upon insertion of the spike means 80 through the stopper, these teeth tend to resist any tendency to accidentally withdraw the spike means from the test tube stopper. A second distinction between the embodiment of FIG. 4 and the embodiment of FIG. 6 is that in the embodiment of FIG. 6, the outlet path bore is curved, or arcuate, as at 84 rather than a straight bore 72 as illustrated in FIG. 4, when considered from the head of the spike to the intersection with a main bore 68. However, a common aspect of the embodiments of FIGS. 4 and 6 is that a portion of the inlet path and a portion of the discharge path are concentric whereas in the embodiments of FIGS. 1 and 2, the inlet path and discharge path are non-concentric.

Each of the puncturing means of FIGS. 2-6 provides a sharpened tip for not only piercing but also for self-centering relative to the stopper. This is an advantage over the configuration of FIG. 1 in that only a single puncture is made in the stopper. In the embodiment of FIG. 1 the body member does tend to seat within the curvature 20 at the top of the stopper or closure.

The bellows, or pump means, is preferably a low density polyethylene while the body member is preferably an impact styrene. In the embodiment of FIG. 1, the needles are metal. The delivery tube may be Teflon, which is a DuPont trademark for a polytetrafluoroethylene.

The foregoing is a complete description of the present invention. Various changes may be made without departing from the spirit and scope of the present invention and thus, it should be appreciated that the present invention has been illustrated and described with numerous embodiments. The invention, therefore, should be limited only by the scope of the following claims.

What is claimed is:

1. Apparatus for transferring fluid from a test tube the test tube having an interior sealed by a resilient self-sealing, reusable, repuncturable closure at one end, said apparatus comprising;

means for puncturing said resilient, self-sealing, reusable closure and for establishing a fluid inlet path and a fluid discharge path, said fluid discharge path having an inside diameter;

delivery means extending through said fluid discharge path, said delivery means having an outside diameter;

means for pressurizing the interior of the test tube for discharging fluid through said delivery means; and means for venting the interior of the test tube, said venting means being such that temperature variations do not cause accidental discharge of the contents of the test tube, said venting means further maintaining sufficient resistance to venting such that the test tube may be pressurized for discharging the contents of the test tube, said venting means for providing continuous venting at least when the interior of the test tube is not pressurized.

2. The invention as defined in claim 1 wherein said venting means includes a clearance which is defined as the region between the exterior of the delivery means and the interior of the fluid discharge path.

3. The invention as defined in claim 1 wherein said venting means includes an aperture in the pressurizing means.

4. The invention as defined in claim 1 wherein said apparatus is self-centering relative to the test tube during puncturing of said closure.

5. The invention as defined in claim 1 wherein said puncturing means punctures said closure in more than one location.

6. The invention as defined in claim 1 wherein said delivery means includes a delivery tube extending through said discharge path.

7. The invention as defined in claim 1 wherein said puncturing means has a plurality of discrete bores therethrough.

8. The invention as defined in claim 1 wherein said puncturing means includes plural, discrete parallel paths therethrough and a single tip for puncturing said test tube closure.

9. The invention as defined in claim 1 wherein at least a portion of the inlet path is concentric with at least a portion of said discharge path.

10. The invention as defined in claim 1 wherein said pressurizing means is a bellows.

11. The invention as defined in claim 1 wherein said pressurizing means is a bellows and said venting means includes an aperture in said bellows.

12. The invention as defined in claim 1 wherein at least a portion of said discharge path is arcuate and at least a portion of said delivery path is concentric with at least a portion of said inlet path.

13. The invention as defined in claim 1 wherein at least a portion of said discharge path is coextensive with at least a portion of said inlet path.

14. The invention as defined in claim 1 wherein said means for establishing said fluid paths includes two spaced apart, hollow cannulas.

15. The invention as defined in claim 1 wherein said means for establishing said fluid paths includes a generally thin, flat, blade-like portion.

16. The invention as defined in claim 1 wherein said means for establishing said fluid paths includes two spaced apart, hollow bores.

17. The invention as defined in claim 1 wherein said means for establishing said fluid paths includes means for resisting removal from said closure.

18. The invention as defined in claim 1 wherein said means for establishing said fluid paths includes locator means for limiting the extent of insertion of the apparatus thereby facilitating automatic loading of a plurality of fluid path establishing means in a plurality of test tubes.

19. Apparatus for transferring fluid from a test tube having an interior sealed by a resilient, self-sealing, reusable, repuncturable closure at one end, said apparatus comprising:

means for puncturing said resilient, self-sealing, reusable closure for establishing a fluid inlet path and a fluid discharge path, said fluid discharge path having an inside diameter;

means for delivering fluid, said fluid delivering means having an outside diameter and extending through said fluid discharge path;

means for pressurizing the interior of the test tube for discharging fluid contents through said delivering means; and means for venting the interior of the test tube, said venting means being configured for preventing accidental discharge of the fluid contents of the test tube when the test tube is subjected to temperature variations, said venting means maintaining sufficient resistance to venting for pressurizing the interior of the test tube for discharging the contents of the test tube, said venting means for providing continuous venting at least when the interior of the test tube is not pressurized.

20. The invention as defined in claim 19 wherein said venting means further includes an aperture in said pressurizing means.

* * * * *